(12) United States Patent
Gewirtz et al.

(10) Patent No.: US 10,646,548 B2
(45) Date of Patent: May 12, 2020

(54) COMPOSITIONS INCLUDING IL-18 AND IL-22 AND THEIR USE IN ANTI-VIRAL THERAPIES

(71) Applicant: Georgia State University Research Foundation, Inc., Atlanta, GA (US)

(72) Inventors: Andrew T. Gewirtz, Smyrna, GA (US); Benyue Zhang, Lilburn, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/028,231

(22) PCT Filed: Oct. 8, 2014

(86) PCT No.: PCT/US2014/059693
§ 371 (c)(1),
(2) Date: Apr. 8, 2016

(87) PCT Pub. No.: WO2015/054386
PCT Pub. Date: Apr. 16, 2015

(65) Prior Publication Data
US 2016/0243195 A1 Aug. 25, 2016

Related U.S. Application Data

(60) Provisional application No. 61/888,439, filed on Oct. 8, 2013.

(51) Int. Cl.
| *A61K 38/20* | (2006.01) |
| *A61K 47/64* | (2017.01) |
| *A61K 47/68* | (2017.01) |
| *A61K 9/00* | (2006.01) |

(52) U.S. Cl.
CPC ............ *A61K 38/20* (2013.01); *A61K 9/0019* (2013.01); *A61K 38/2006* (2013.01); *A61K 47/643* (2017.08); *A61K 47/6813* (2017.08)

(58) Field of Classification Search
None
See application file for complete search history.

(56) References Cited

U.S. PATENT DOCUMENTS

| 2007/0009926 A1* | 1/2007 | Veas ............... A61K 38/08 435/5 |
| 2009/0202475 A1* | 8/2009 | Abbas ............. A61K 38/1709 424/85.2 |
| 2010/0061958 A1 | 3/2010 | Carroll et al. |
| 2012/0258126 A1 | 10/2012 | Scholler et al. |

FOREIGN PATENT DOCUMENTS

| CA | 2662609 A1 | 3/2008 |
| EP | 2633865 A1 | 9/2013 |
| WO | 2009/100035 A2 | 8/2009 |
| WO | 2010/037402 A1 | 4/2010 |

* cited by examiner

*Primary Examiner* — Dong Jiang
(74) *Attorney, Agent, or Firm* — Meunier Carlin & Curfman LLP

(57) ABSTRACT

The present invention is directed to compositions including the cytokines IL-18 and IL-22 or biologically active fragments or variants thereof. In some embodiments, the compositions further include a pharmaceutically acceptable carrier. The compositions can further include other interleukins such as IL-1β, and IL 1β can be used as a combination therapy with either IL-18 or IL-22 or biologically active fragments or variants thereof.

5 Claims, 7 Drawing Sheets

F

Small intestine

G

The Y axis is Fecal Rotavirus Shedding (SD50/100mg feces)

Days p.i.

E

F

COMPOSITIONS INCLUDING IL-18 AND IL-22 AND THEIR USE IN ANTI-VIRAL THERAPIES

CROSS-REFERENCE TO RELATED APPLICATIONS

This application is a U.S. National Stage Application of International Application No. PCT/US2014/059693, filed on Oct. 8, 2014, which claims the benefit of the filing date of U.S. Provisional Application No. 61/888,439 filed on Oct. 8, 2013. The entire content of these earlier-filed applications is hereby incorporated by reference herein.

FIELD OF THE INVENTION

The present invention relates to compositions (e.g., pharmaceutical compositions or physiologically acceptable compositions) that include a combination of the interleukins IL-18 (interleukin-18), IL-22 (interleukin-22), and IL-1β (interleukin-1β). For example, the composition can include both IL-18 and IL-22, and the invention features the use of IL-18 and IL-22 in the preparation of a medicament. Methods of making such compositions and their use in the treatment of microbial infections (e.g., bacterial or viral infections) are also within the scope of the present invention.

BACKGROUND

Rotavirus (RV) causes severe dehydrating diarrhea in young children and moderate intestinal distress in adults (Greenberg et al., *Gastroenterol.* 136:1939, 2009). Analogously, RV infection of adult mice does not result in watery diarrhea but, rather, serves as a well-defined model of intestinal viral infection in which infectivity can be monitored by measuring levels of viral antigen shed in feces (Feng et al., *Adv. Exp. Med. Biol.* 412:233, 1997). RV predominantly infects and replicates in epithelial cells lining the small intestine (Sen et al., *J. Virol.* 83:10322, 2009). Bacterial flagellin, the primary component of bacterial flagella, directly and potently activates host defense gene expression in intestinal epithelial cells (IEC) (Zeng et al., *J. Immunol.* 171:3668, 2003) and, moreover, has been suggested to be a major target of innate and adaptive immunity in the intestine (Vijay-Kumar and Gewirtz, *Mucosal Immunol.* 2:197, 2009). The specific pattern of gene expression induced by flagellin in IEC can be viewed as an NF-κB-mediated transcriptional response highly reminiscent of that induced by bacterial pathogens such as *Salmonella* species and differs strikingly from that induced by RV, its components, or the viral dsRNA mimetic poly-(I:C), which induces a type I interferon-mediated antiviral response (Frias et al., *Mucosal Immunol.* 3:622, 2010; Vijay-Kumar et al., *J. Immunol.* 174:6322, 2005). Such flagellin-induced gene expression confers both IEC and mice with resistance to a variety of challenges including bacteria, chemicals, and radiation (Jones et al., *Gut* 60:748, 2011; Burdelya et al., *Science* 320:226, 2008; Jarchum et al., *Infect. Immun.* 79:1498, 2011; and Kinnebrew et al., *J. Infect. Dis.* 201:534, 2010). Moreover, and although flagellin does not induce expression of genes recognized to have antiviral activity, administration of flagellin reduced susceptibility of mice to a culture-adapted strain of RV (Vijay-Kumar et al., *J. Immunol.* 180:8280, 2008).

SUMMARY

The present invention is based, in part, on our work using flagellin to protect against RV (rotavirus) infection in wild-type and immunocompromised mice. Our studies show that flagellin treatment can inhibit RV infection in young mice and in immunocompromised mice with almost no detectable antibody response to the virus. Because our research indicates that the antiviral effect of flagellin treatment is attributable to signaling pathways that lead to the production of IL-18, IL-22, and IL-1β, we have further tested these interleukins as anti-viral agents, and the present invention features compositions and methods for treating viral infections by administering a combination of these interleukins (e.g., a combination of the interleukins IL-18 and IL-22) and/or biologically active fragments or variants thereof. The invention also features methods of administering the compositions described herein to a subject (e.g., a human patient) for the treatment of a microbial infection (e.g., a viral infection) and the use of the combined (e.g., co-formulated) interleukins in the preparation of a medicament. We use the terms "subject" and "patient" interchangeably to refer to a living being for whom the present compositions are prescribed or to whom the present compositions can be administered. Although human beings are clearly intended subjects or patients, the invention is not so limited. Veterinary use is also contemplated, particularly for domesticated animals. We may use the term "patient" to describe a subject who has been diagnosed as having an infection (i.e., a subject who is symptomatic and/or has tested "positive" for a microbial infection). Similarly, we may use the term "subject" to describe a living being who has not yet been diagnosed as having an infection (i.e., a person or other subject who is asymptomatic but determined to be at risk for infection due, for example, to a heightened risk of exposure to a microbe (due, for example, to impending travel to a region where infections are more common).

Accordingly, in a first aspect, the present invention is directed to compositions including the cytokines IL-18 and IL-22 or biologically active fragments or variants thereof. In some embodiments, the compositions further include a pharmaceutically acceptable carrier. The compositions can further include other interleukins such as IL-1β, and IL-1β can be used as a combination therapy with either IL-18 or IL-22 or biologically active fragments or variants thereof. For ease of reading, we do not repeat the phrase "or a biologically active fragment or variant thereof" at every opportunity. It is to be understood that where some combination of IL-18, IL-22, and IL-1β is made or used, biologically active fragments or variants of these cytokines can also be made or used. More specifically, the present compositions can include IL-18 and IL-22; IL-18 and IL-22 and IL-1β; IL-18 and IL-1β; or IL-22 and IL-1β. Any of the interleukins, regardless of the particular manner in which they are combined, packaged, or used, can be synthesized, recombinantly produced, or isolated from a natural source (e.g., a human or other mammal). Thus, the interleukins can be human interleukins.

Any interleukin within a composition (e.g., a pharmaceutical composition; i.e., any combination of IL-18, IL-22, and IL-1β or a biologically active fragment of these cytokines) can be further defined by the inclusion of a heterologous polypeptide that increases the circulating half-life of the interleukin to which it is joined. The heterologous polypeptide can be, for example, an albumin, transferrin, t-PA, or any other protein with a sufficiently long circulating half-life that it improves the circulating half-life of the cytokine to which it is attached. The heterologous polypeptide can also be a portion of an immunoglobulin that lacks an antigen-binding region.

The compositions of the invention (e.g., pharmaceutical or physiologically acceptable compositions) can be formulated for oral or parenteral (e.g., intravenous, subcutaneous, or intraperitoneal) administration.

A fragment or variant of a given interleukin (e.g., IL-18, IL-22, or IL-1β) can be at least or about 70% (e.g., at least or about 75%, 80%, 85%, 90%, 95%, or 98%) identical to the corresponding wild type interleukin.

In another aspect, the invention is directed to compositions including one or more nucleic acids that encode IL-18, IL-22, or IL-1β (either alone or in any combination), or a biologically active fragment or variant thereof. The nucleic acid sequence can further encode a heterologous polypeptide that increases the circulating half-life of the interleukin to which it is joined (including the heterologous polypeptides described above or elsewhere herein).

The nucleic acid can be contained with a vector, such as an expression vector derived from a bacterium, virus, or plasmid), and compositions comprising such nucleic acids can be formulated for use in treating the patients described herein (e.g., by parenteral administration, such as intravenous, subcutaneous, or intraperitoneal administration).

In another aspect, the invention is directed to an isolated cell that includes a nucleic acid sequence as described herein (e.g., one encoding an interleukin such as IL-18, IL-22, or IL-1β, or a combination thereof, either alone or fused to a heterologous polypeptide that increases circulating half-life). Bacterial cells in culture are "isolated," as are cells from higher organisms that are no longer associated with their natural environment.

In another aspect, the invention is directed to methods of treating a microbial infection (e.g., a viral infection) in a subject (e.g., a human patient or other mammal). The methods can include a step of identifying a subject or patient in need of treatment (e.g., an infant, child, or an adult, including patients that require treatment for an acute and/or chronic viral infection or patients with a compromised immune system) and can include a step of administering to the subject or patient a therapeutically effective amount of a pharmaceutical composition that includes a combination of interleukins as described herein (e.g., IL-18, IL-22, and IL-1β or combinations thereof) or biologically active fragments or variants thereof. The invention can also be expressed in terms of the "use" of the presently described interleukins in the preparation of a medicament (e.g., the preparation of a medicament for the treatment of a microbial infection (e.g. a viral infection) or the prophylaxis of such infections).

The subject may or may not exhibit signs or symptoms of a viral infection. In some aspects of the invention, the compositions may be administered to a subject post-infection, upon diagnosis of an infection, prophylactically, or to patients with chronic viral infections. The present compositions, methods, and uses can be applied where the microbial agent is a virus of the reoviridae family, including viruses that can affect the gastrointestinal system, such as rotavirus (including an influenza virus, a herpes virus, a hepatitis virus, or a lentivirus), an RNA virus (including diseases such as SARS, influenza, hepatitis C, West Nile fever, polio, and measles), a DNA virus (including diseases such as smallpox, chickenpox, and shingles), or a retrovirus (such as including the HIV virus; and including diseases such as AIDS associated with an HIV infection, tumors, and autoimmune disease). In one embodiment, the subject or patient is immunocompromised.

In another aspect, the invention also features methods of treating a viral infection that further includes administering to a patient in need of treatment a pharmaceutical composition that includes a nucleic acid that encodes interleukins such as IL-18, IL-22, and IL-1β or biologically active fragments or variants thereof. In some embodiments, the pharmaceutical compositions described herein may be administered in combination with one or more antiviral agents (exemplary agents are provided further below).

The term "biologically active" with respect to the interleukins described herein means an analog or fragment of a given interleukin that retains sufficient activity, such as receptor binding affinity in a physiological setting, to be considered effective and useful. A fragment or variant of IL-18, IL-22, or IL-1β is "biologically active" when it promotes resistance to rotavirus infection or reduces rotavirus levels (for example, to the extent IL-22 and IL-18 do so in an experimental model as described in the Examples). A "fragment" of a given interleukin protein is a continuous or contiguous portion of the given interleukin protein (e.g., a fragment of a polypeptide that is ten amino acids long can be any 2-9 contiguous residues within that interleukin protein). An "analog" or "variant" of a given interleukin protein is any protein having an amino acid sequence that is similar to, but not identical to, the sequence of a given interleukin protein. Thus, a protein that includes one or more amino acid substitutions, additions, or deletions of any amino acid residue (or any combination thereof) is an analog of the referenced interleukin protein, and a fragment is a type of analog.

By "about" we mean within a range of plus-or-minus 10% of a referenced value. For example, about 10 mg means 9-11 mg. Where ranges are provided or contemplated (e.g., by the use of the term "about" or "between") it is to be understood that the end points of the range are useful values within the context of the invention.

BRIEF DESCRIPTION OF THE DRAWINGS

(FIG. 1D). Total RNA from small intestines of those mice was prepared and analyzed for RV NSP3 RNA level (Student t-test, N=6, *P<0.05; FIG. 1E). Three-week-old RAG1$^{-/-}$ mice were inoculated with murine RV. Three weeks following inoculation, at which point a chronic infection had been established, mice were treated with PBS or flagellin (20 μg) every second day from 22-40 days p.i. as indicated by arrows along the X-axis (FIG. 1E). Feces were collected on the days indicated and assayed for RV antigens by ELISA. The difference between mice given PBS and flagellin was statistically significant (mean+/−S.E.M, 2-way ANOVA, N=5, P<0.0001) (FIGS. 1F and 1G). Chronically RV-infected RAG1$^{-/-}$ mice were administered 1 dose of flagellin, euthanized at 3, 6, 12, 24 and 48 hours (FIG. 1F). Total RNA of small intestines were analyzed for NSP3 RNA level and ratio of positive strand to negative strand of NSP3 by strand-specific qRT-PCR. Total RNA of liver were also analyzed for RV NSP3 RNA level [Student t-test, N=3, *P<0.05, for (F) and (G)] (FIG. 1G).

in FIG. 3A, IFN I R$^{-/-}$, in FIG. 3B IFNγR1$^{-/-}$, in FIG. 3C, IFN I & II R$^{-/-}$, in FIG. 3D, STAT1$^{-/-}$, in FIG. 3E, p40$^{-/-}$, in FIG. 3F, RAG2/IL-2Rγ$^{-/-}$ mice, in FIG. 3G, WT C57BL/6 mice treated with IL-17 neutralizing mAb, in FIG. 3H, IL-22$^{-/-}$, in FIG. 3I, WT C57BL/6 mice treated with IL-22 neutralizing mAb, in FIG. 3J, in FIG. 3K, IL-18BP TG, and in FIG. 3L, IL-18$^{-/-}$ mice. The results are shown as mean+/−S.E.M (N=4-6). The differences between mice given PBS and flagellin were statistically significant for FIG. 3A to FIG. 3D, FIG. 3G, and FIG. 3J (2-way ANOVA, P<0.0001) and significant at individual days of FIG. 3E, FIG. 3F, FIG. 3H, FIG. 3I, FIG. 3K, and FIG. 3L (Student's t-test, P<0.05 on day 3 in (FIG. 3E), days 7 and 9 of (FIG. 3F), day 5 of (FIG. 3H), day 7 of (FIG. 3I), days 3-4 in (FIG. 3K) and days 3-4 in (FIG. 3L)).

FIG. 4D is a Venn diagram representation of IL-18, IL-22 and IL-22/IL-18 treatment on intestinal epithelial cell gene expression. Total mRNA from IECs of mice treated with the indicated cytokines was assayed for RNA sequencing. Genes with significantly modified expression (up or down) in a treated group compared to a control group were determined by exact test function of EdgeR using the exact negative binomial test. Whole cell lysates from the IECs described above were analyzed by SDS-PAGE immunoblotting with antibodies to cleaved caspase 3. The left-hand panel of FIG. 4E shows the results 3 hours after the different cytokine treatments and the right-hand panel shows the results at the indicated time points (0, 3, 6, and 24 hours) of IL-22/IL-18 treatment. Total RNA from the IECs was analyzed for NSP3 RNA level and the ratio of positive strand to negative strand of NSP3 by strand-specific-qRT-PCR. The differences between PBS-treated and cytokine-treated groups are shown in the left-hand panel of FIG. 4F (Student t-test, N=4, *P<0.001 for RV genome, *P<0.05 for RV RNA+/−strand ratio). Total RNA analyzed at the indicated time points was also analyzed for levels of RV NSP3 RNA. The differences between PBS-treated and cytokine-treated groups are shown in the right-hand panel of FIG. 4F (Student t-test, N=4, *P<0.0001).

DETAILED DESCRIPTION

Figure 1:
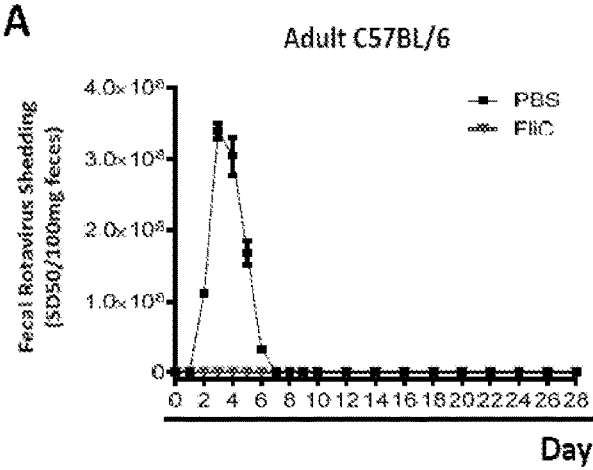
FIGS. 1A-1G are graphs illustrating data indicating that flagellin protects mice from RV infection and diarrhea. Adult (eight-week-old) female C57BL/6 mice (FIG. 1A) or RAG1$^{-/-}$ mice (FIG. 1B) were orally inoculated with murine RV, EC strain. Mice were administered 0.2 ml PBS (vehicle) or 0.2 ml PBS containing 20 μg of flagellin (FliC) by intraperitoneal (i.p.) injection, and then every 2nd day from 0-18 days post-infection (p.i.). Feces were collected daily and assayed for RV antigens by ELISA. Results are shown as mean+/−S.E.M. The difference between mice given PBS and flagellin was statistically significant [2-way ANOVA, N=4, P<0.001 for (A) and (B)]. Neonatal (seven-day old) C57BL/6 mice were orally inoculated with RV as described in the Examples (FIG. 1C). Mice were treated with PBS or flagellin (10 μg) every day from 0-9 days p.i. and monitored for incidence of diarrhea daily (Chi-square test, N=11, *P<0.01). Flagellin-treated mice exhibited significantly reduced duration of diarrhea and days of active diarrhea (Student t-test, N=11, *P<0.01). Seven-day old mice, treated as described for FIG. 1C, were euthanized 3 days p.i.
Figure 1:
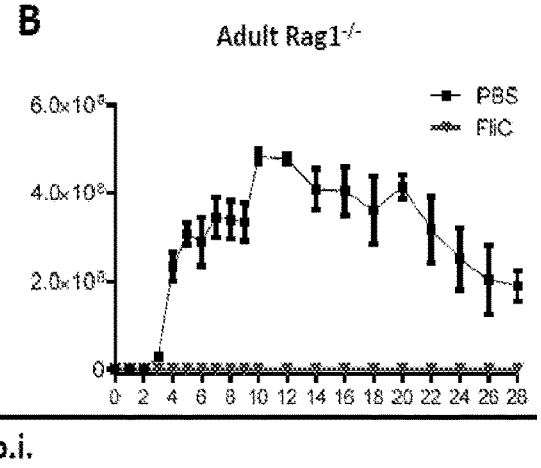
Figure 1:
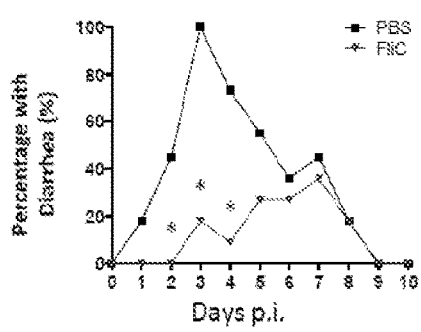
Figure 1:
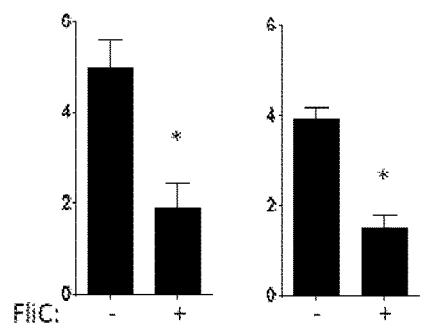
Figure 1:
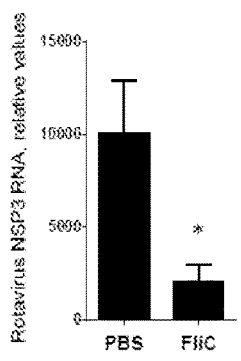
Figure 1:
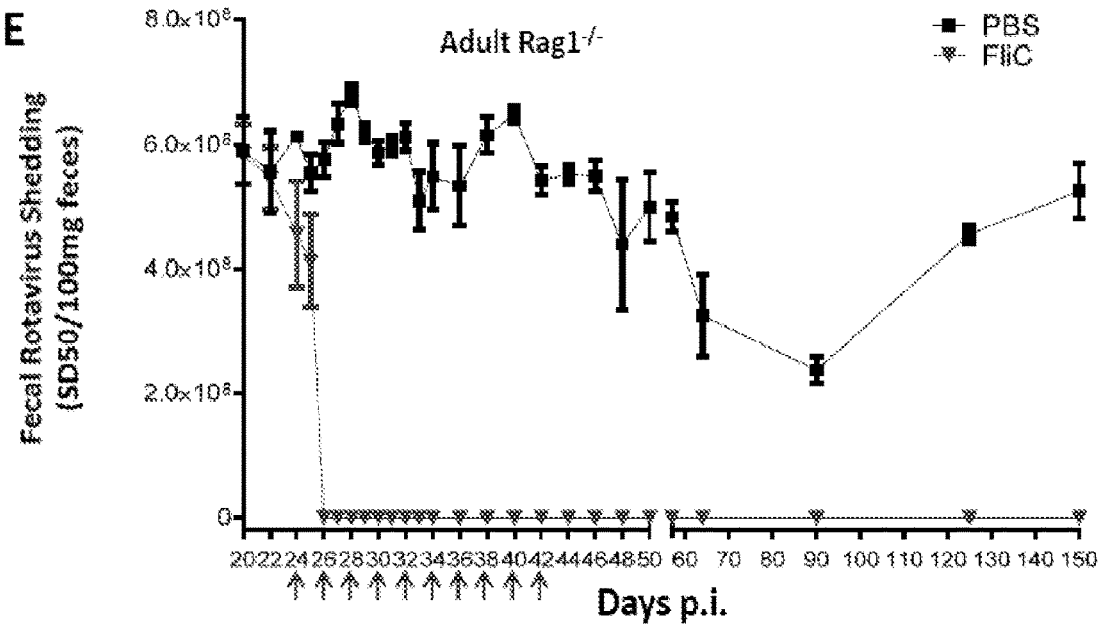
Figure 1:
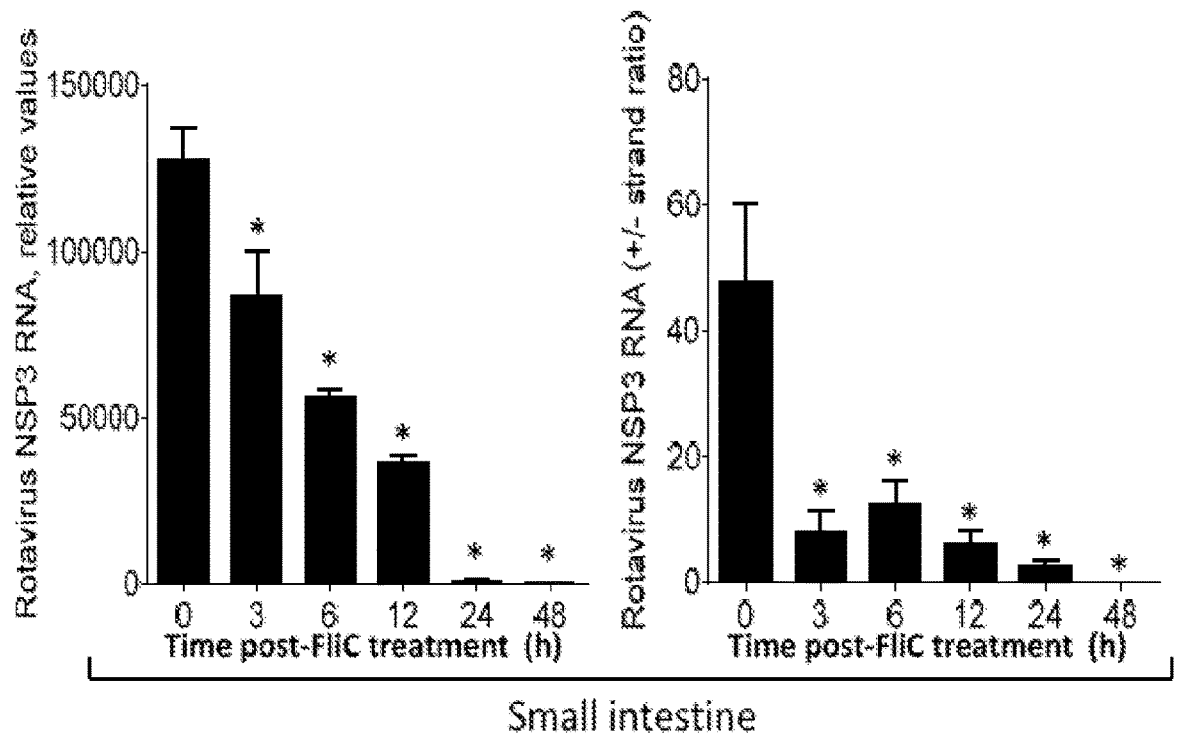
Figure 1:
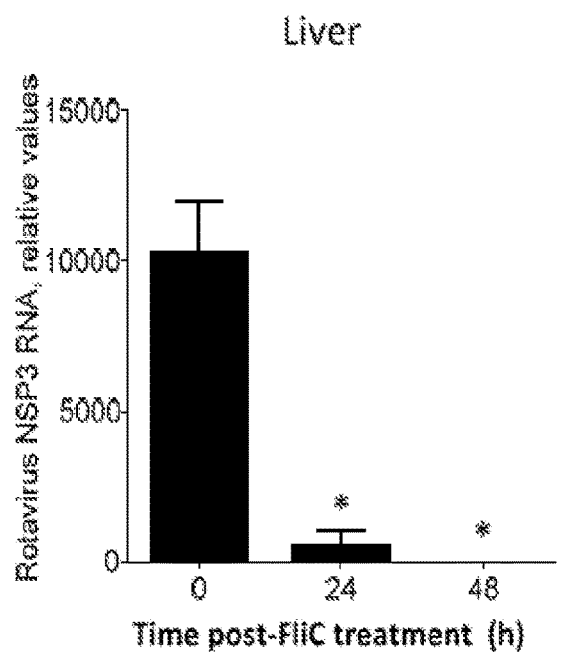

Viral infections, many of which cannot be prevented or treated, cause and/or promote many of the most pressing health problems in the world. Consequently, we have been investigating strategies to prevent and/or treat viral and other microbial infections. While the invention is not limited to compositions and methods that achieve clinically beneficial results by any given mechanism, we expect the results to date have been achieved by activating endogenous pathways of innate immunity, and we have focused on the administration of the bacterial protein flagellin or the combinations of interleukins, including the pro-inflammatory cytokines IL-18 and IL-1β, specified herein. Using murine rotavirus (RV) infection as a model of an acute diarrhea-inducing infection in young mice and a chronic infection in immune-deficient mice, we observed flagellin treatment could prevent or eliminate ongoing RV infection. Such protection was independent of adaptive immunity and interferon (type I and II), which is thought to be the major mediator of antiviral immunity, while requiring both known flagellin receptors, toll-like receptor 5 (TLR5) and Nod-like receptor C4 (NLRC4), whose expression by dendritic cells was necessary and sufficient to mediate flagellin-induced protection against RV. We have found that flagellin-mediated blockade of infection dramatically attenuates the severe diarrhea induced by RV in young mice. Our studies with flagellin indicate that IL-22 is necessary for the antiviral effect and suggest that IL-18 and IL-1B may also be needed. In subsequent work, we attempted to recapitulate flagellin's antiviral effect (which induces up to perhaps 50 different cytokines) with certain combinations of these interleukins (including a combined treatment with IL-22 and a pro-inflammatory cytokine such as IL-18 and/or IL-1β). We were surprised to find that a combination of IL-18 and IL-22 reduced viral load to the same extent as flagellin and IL-18, IL-22, and IL-1β resulted in a complete eradication of chronic rotavirus infection. None of these cytokines are sufficient by themselves to cure the infection.

Interleukins useful in the present compositions and methods: First, with regard to source, any of the interleukins described herein can be purified from any given source (e.g., a naturally occurring source or an expression system); may have the sequence of a naturally expressed interleukin (for example, the sequence of an IL-18, IL-22, or IL-1β expressed by a human or other mammal (these sequences are known in the art and readily obtainable); and may be post-translationally modified in any manner that enhances or allows the polypeptide to retain the ability to achieve a clinically beneficial result when used as described herein. For example, the modification may enhance or retain the polypeptide's ability to attenuate diarrhea associated with a microbial infection. The post-translational modification can be, for example, an acylation (e.g., O-, N-, or S-acylation), formylation, alkylation (e.g., by addition of a $C_1$-$C_6$ carbon), glycosylation, hydroxylation, iodination, oxidation, biotinylation, pegylation, thiolation, or phosphorylation.

IL-18, which is also referred to as interferon-gamma inducing factor and which is useful in the compositions, methods, and uses of the invention, is a cytokine protein encoded by the IL-18 gene. It has proinflammatory biological activities and belongs to the IL-1 superfamily. Recombinant forms are available. For instance, recombinant human IL-18 is generated in *Escherichia coli* and is a 157-amino acid protein of 18 kDa.

IL-22 is a cytokine protein encoded by the IL-22 gene. It has an α-helical structure and belongs to the IL-10 superfamily of cytokines. It plays an important role in mediating inflammatory responses at the cellular level by initiating biological activity through binding to IL-22R1 and IL-10R2. Recombinant human IL-22 is a homodimeric polypeptide (292 amino acids), and can also be produced in bacterial cell cultures, including cultures of *Escherichia coli*. In its non-glycosylated form, recombinant human IL-22 has a molecular weight of 34 kDa. Other recombinant IL-22 protein fragments are available such as a chicken IL-22 protein fragment produced in yeast.

IL-1β (also referred to as catabolin) is a cytokine protein encoded by the IL-1β gene with a molecular weight of 17.5 kDa. IL-1β belongs to the IL-1 family of cytokines and binds the IL-1 receptor. Like IL-18 and IL-22, IL-1β plays an important role in the proinflammatory response. IL-1β (163-171 amino acids) has been shown to be biologically active on hormone release in bovine granulosa cells. Recombinant human IL-1β fragments are available, such as human recombinant IL-1β (117-269 amino acids) generated in *Escherichia coli*.

The in vivo half-life of an interleukin as described herein can be increased by bonding (e.g., covalently bonding) the interleukin (directly or via a linker or spacer) to a heterologous polypeptide, which may be biologically inactive in the subject or patient to whom the modified interleukin is administered. The inactivity can arise naturally (i.e., the heterologous polypeptide may simply not be active in the patient to whom it is administered). For example, the heterologous polypeptide can be a plant enzyme or an enzyme from a non-human genus (e.g., a porcine or murine galactosyltransferase (e.g., α-1,3-galactosyltransferase) that is not active in a human subject or patient) (see Sandrin et al., *Proc. Natl. Acad. Sci. USA* 90:11391, 1993). The inactivity can also be engineered by introducing one or more mutations into the heterologous polypeptide (e.g., sequences may be deleted that are required for activity, nevertheless leaving the heterologous polypeptide large enough to increase the circulating half-life of an interleukin (e.g., IL-18, IL-22, or IL-1β) to which it has been joined). Preferably, the circulating half-life of the interleukin will increase in vivo by a factor of at least two and preferably by a factor of at least 5-10 or more (e.g., at least or about a factor of 20). The heterologous polypeptide can be, for example, albumin (e.g., human serum albumin), transferrin, an enzyme such as t-PA, or any other protein with a long circulating half-life and without unwanted (i.e., deleterious) enzymatic or biologic activity in a patient (e.g., a human patient). The heterologous polypeptide can also be a portion of an immunoglobulin that does not bind a target (e.g., a target antigen or immunogen). For example, the heterologous polypeptide can be an immunoglobulin that lacks antigen-binding sites or includes mutated or otherwise disabled antigen-binding sites. More specifically, the heterologous polypeptide can be or can include the hinge region or Fc region of an immunoglobulin (e.g., an IgG). Where the hinge region is included, it can serve as a flexible spacer between the interleukin (e.g., IL-22, IL-18, or IL-1β) and the half-life-increasing polypeptide (e.g., an IgG Fc or albumin). Where an Fc region is incorporated, it can include a mutation that inhibits complement fixation and prevents the Fc region from binding the Fc receptor with high affinity (thus preventing the polypeptide from being lytic). In murine IgG Fc regions, substituting Glu 318, Lys 320, and Lys 322 with alanine residues renders the protein unable to direct ADCC. Substitution of Glu for Leu 235 inhibits the ability of the protein to bind the Fc receptor with high affinity. Comparable mutations can be made in human or other immunoglobulins, and suitable mutations for human IgGs also are known (see, e.g., Morrison et al., *The Immunologist* 2:119-124, 1994; and Brekke et al., *The Immunologist* 2:125, 1994). Other mutations can also be used to inhibit protein activity, and art-recognized methods can be used to assay for the ability of the protein to fix complement or bind the Fc receptor.

Interleukin fragments relate to a portion of a full-length amino acid or nucleic acid sequence (e.g., any sequence described herein). In other words, when we refer to a biologically active fragment of IL-18, IL-22, or IL-1β, we may be referring to a biologically active fragment of the polypeptide or a nucleic acid sequence that encodes it. Fragments may constitute at least or about 50%, 60%, 70%, 80%, 85%, 90%, 95%, 98% or 99% of the corresponding full length sequence. In terms of absolute numbers, fragments may include at least or about 4, 5, 6, 8, 10, 11, 12, 14, 15, 16, 17, 18, 20, 25, 30, 35, 40, 45, or 50 amino acids or nucleic acids of the corresponding full length sequence. As noted above, biologically active fragments or other variants of IL-18, IL-22, and IL-1β can be used in the present invention in place of, or in addition to, their wild type counterparts, and they are biologically active when they promote resistance to rotavirus infection or reduce rotavirus levels (for example, to the extent IL-22 and IL-18 do so in an experimental model as described in the Examples).

Nucleic acids, vectors, and cells expressing one or more interleukins as described herein: In certain aspects of the invention, compositions including nucleic acids that encode the interleukins described herein may also be made, packaged, and administered. A vector (e.g., an expression vector) may encode the interleukins or biologically active fragments or variants thereof or may include a therapeutic nucleic acid. Nucleic acids include any type of nucleic acid known in the art, such a double- and single-stranded DNA and RNA molecules of any length, conformation, charge, or shape/configuration (i.e., linear, concatemer, circular (e.g., a plasmid), nicked circular, coiled, supercoiled, or charged). Additionally, the nucleic acid can contain 5' and 3' terminal modifications and can include blunt and/or overhanging nucleotides at these termini, or combinations thereof. The nucleic acid can be, for example, a DNA molecule, an RNA molecule, or a modified form thereof.

Transport vectors are capable of binding or containing a pharmaceutical composition or therapeutic agent including the interleukins or biologically active fragments or variants thereof and heterologous polypeptide disclosed herewith. Transport vectors may be any compound or composition such as a lipid, carbohydrate, polymer or surfactant that may be capable of transporting the pharmaceutical composition or therapeutic agent, such as a small molecule drug. Preferred transport vectors include lipid micelles, liposomes, lipoplexes, dendrimers, and nanoparticles. The transport vector may contain the pharmaceutical composition or interleukin cytokines. Alternatively, the transport vector may be connected to or linked to the interleukin protein or heterologous polypeptide.

Methods of making: The polypeptides described herein can be expressed (e.g., in mammalian cells (e.g., human cells) or bacterial cells (e.g., *E. coli*) using conventional methods for protein expression and using recombinant DNA technology that is well known in the art of molecular biology. Because IL-18, IL-22, IL-1β, and many of the polypeptides useful in increasing the circulating half-life of these polypeptides have been previously purified, many of the previously described methods of protein purification, along with other conventional methods, should be useful in purifying polypeptides for the present compositions and methods. If desired, the interleukins and chimeric proteins of which they are a part can be affinity-purified according to standard protocols with antibodies directed against the interleukin. Antibodies directed against the heterologous polypeptide are also useful for purifying chimeric proteins by conventional immunoaffinity techniques. If desired, the activity of a chimeric protein can be assayed with methods that are commonly used to test the activity of the interleukin alone. It is not necessary that the activity of the chimeric interleukin be identical to the activity of the interleukin alone; it may be more or less active, so long as the level of activity achieves a desirable therapeutic outcome.

Pharmaceutical compositions: The present invention is also directed to pharmaceutical compositions that contain a therapeutically effective amount of the cytokines as described herein. The compositions can be formulated for administration by any of a variety of routes of administration, and can include one or more physiologically acceptable excipients, which may vary depending on the route of administration. The term "excipient" is used broadly to mean any compound or substance, including those that may also be referred to as "carriers" or "diluents." Preparing pharmaceutical and physiologically acceptable compositions is generally considered to be routine in the art, and one of ordinary skill in the art can consult numerous authorities for guidance. For example, one can consult Remington's Pharmaceutical Sciences, Mack Publishing Company, Philadelphia, Pa., $17^{th}$ Ed., 1985.

The pharmaceutical compositions of the present invention can be prepared for oral or parenteral administration. Oral administration is advantageous in that it is simple and patient compliance is high. Parenteral administration may be preferred to avoid the challenges of administering a protein-based active agent orally. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration with intravenous and subcutaneous routes of administration being preferred. Thus, the invention provides compositions for parenteral administration that include the interleukins described herein dissolved or suspended in an acceptable carrier (a term we use to refer to any non-toxic substance that can be formulated with the interleukins described herein to generate a pharmaceutically acceptable formulation), preferably an aqueous carrier, such as water, buffered water, saline, buffered saline (e.g., PBS), and the like. One or more of the excipients included may help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions may be sterile. For example, they may be sterilized by conventional sterilization techniques or may be sterile filtered. Aqueous solutions may be packaged for use as is, or lyophilized, and the lyophilized preparation, which is encompassed by the invention, can be combined with a sterile aqueous carrier prior to administration. The pH of the pharmaceutical compositions typically will be between 3 and 11 (e.g., between about 5 and 9) or between 6 and 8 (e.g., between about 7 and 8). In some embodiments, the pH of the pharmaceutical compositions is between about 7.0 and 7.5. The resulting compositions in solid or liquid form may be packaged in multiple single dose units, each containing a fixed amount of the above-mentioned agent or agents, such as in a sealed package of tablets or capsules. Packages comprising multiple single dose units are within the scope of the present invention and may include product literature and/or instructions for use. The composition in solid form can also be packaged in a container for a flexible quantity, such as in a squeezable tube designed for a topically applicable cream, gel, or ointment. Unit dosages may contain between 0.1 and 1000 mg, and usually between 5 and 500 mg, of the at least one interleukin of the invention (e.g., about 0.1, 0.2, 0.4, 0.5, 0.6, 1.0, 2, 5, 10, 25, 50, 100, 200, 300 or 400 mg per unit dosage). For example, where the composition (e.g., a pharmaceutical or physiologically acceptable composition) includes IL-18 and IL-22, a unit dosage form of the composition can include between about 0.1 and 1,000 mg of each interleukin (e.g., about 0.1, 0.2, 0.4, 0.5, 0.6, 1.0, 2, 5, 10, 25, 50, 60, 100, 200, 300 or 400 mg of each of IL-18 and IL-22 per unit dosage). For example, a unit dosage form can include between about 0.1 (e.g. about 0.5) and 50 (e.g., about 35) mg of IL-18 and between about 0.1 (e.g., about 0.5) and 50 (e.g., about 35) mg of IL-22. Where IL-1β is also included, it may be included in the unit dosage form in an amount between about 0.1 and 1,000 mg (e.g., about 0.1, 0.2, 0.4, 0.5, 0.6, 1.0, 2, 5, 10, 25, 50, 60, 100, 200, 300 or 400 mg per unit dosage). Where a patient's weight is above an average of about 140 pounds (63 kg), or where the symptoms of infection are severe, the unit dosage may be increased or more than one unit dosage may be administered at a time or over the course of a day. The data we have obtained to date indicate that differing amounts of IL-18 and IL-22 can be therapeutically effective amounts. For example, the ratio of IL-18:1-22 can be about 1:2, 1:5, 1:10, 1:20, 1:25, 1:50 or 1:100.

The pharmaceutical compositions may be administered in combination with a second or more (e.g., a third or fourth) antimicrobial (e.g., antiviral) agent. More specifically, any combination of the IL-18, IL-22 and IL-1β interleukins (i.e., IL-18+IL-22; IL-18+IL-22+IL-1β; IL-18+IL-1β; or IL-22+IL-1β) may be administered to a patient in need of treatment in combination with one or more of the following antiviral agents: abacavir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuriding, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu™), peginterferon α-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex™), balganciclovir, vicriviroc, vidarabine, viramidine zalcitabine, zanamivir (Relenza™), and/or zidovudine (AZT). More generally, antiviral agents including, but are not limited to, protease inhibitors (PIs), integrase inhibitors, entry inhibitors (fusion inhibitors), maturation inhibitors, reverse transcriptase inhibitors (antiretrovirals), nucleoside and nucleotide reverse transcriptase inhibitors (NRTI) and/or a non-nucleoside reverse transcriptase inhibitor (an NNRTI) can be used in combination with (either formulated with or co-administered with) the combinations of interleukins described herein (e.g., IL-18 and IL-22).

The pharmaceutical compositions will be administered in an "effective amount" (i.e., the amount of the composition that upon administration is sufficient to achieve the desired therapeutic or prophylactic effect in the subject or patient). The amount(s) to be administered, the route of administration and the further treatment regimen may be determined by the treating physician, nurse practitioner, or other qualified healthcare provider, depending on factors such as the age, gender and general condition of the patient and the nature and severity of the disease/symptoms to be treated.

Formulations: The interleukins described herein can be administered as a combination therapy either by virtue of being administered together within the same formulation (and may even be further associated by virtue of inclusion within the same fusion protein or a nucleic acid encoding same) or in separate formulations that are administered simultaneously or sequentially by the same or different routes of administration. For example, a patient can receive two injections, the first including IL-18 and the second including IL-22 by the same or different routes (e.g., both can be administered intravenously; both can be administered subcutaneously; or one can be administered intravenously while the second is administered subcutaneously). For subcutaneous or intravenous administration, the compositions may be prepared according to techniques and methods well known in the art of pharmaceutical formulation and with substances customarily included as solubilizers, emulsifiers or further auxiliaries brought into a solution, suspension, or emulsion. The compositions can also be lyophilized and the lyophilizates obtained can be used, for example, in the production of injection or infusion preparations. Suitable solvents such as water, physiological saline solution or alcohols (e.g., ethanol, propanol, glycerol), sugar solutions such as glucose or mannitol solutions, or mixtures of the various solvents may be used. The injectable solutions or suspensions may be formulated according to methods known in the art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Other routes of administration, including intraperitoneal and nasal/inhalation, are known in the art and are within the scope of the present invention.

Methods of treatment and use: The methods of treatment can be carried out by administering to a patient in need of treatment, a pharmaceutical composition comprising IL-18 and IL-22 or a biologically active fragment or variant thereof and a pharmaceutically acceptable carrier. The method of treatment may further comprise IL-1β or a biologically active fragment or variant thereof (or, IL-1β can be used in place of IL-18 or IL-22). The method of treatment may, alternatively or in addition, include a pharmaceutical composition comprising a nucleic acid encoding any combination of the interleukins disclosed herewith. An additional method of treatment step may include the administration of the pharmaceutical compositions described herein along with one or more antiviral agents. The antiviral agents may be given together with, before, or after the pharmaceutical compositions including the interleukins disclosed herein. In some aspects of the invention, the method may also include serological monitoring of the subject or patient.

The pharmaceutical compositions described herein may be used to treat a variety of diseases and conditions that are linked to microbial (e.g., viral) exposure or microbial (e.g., viral) infection in a subject or patient. The compositions, methods, and uses can also be employed where there is a suspicion or expectation of microbial (e.g., viral) exposure, as may occur in regions where a known outbreak has been recognized or when healthcare workers, travelers, or others are expected to encounter an environment where the risk is heightened. The subject may or may not exhibit signs or symptoms of a viral infection in order for treatment to commence. In various embodiments of the invention, the composition may be administered to a subject or patient post-infection, upon diagnosis of an infection, prophylactically, or in subjects or patients with chronic viral infections. The present compositions, methods, and uses can be applied where the microbial agent is a virus of the reoviridae family, including viruses that can affect the gastrointestinal system, such as rotavirus (including an influenza virus, a herpes virus, a hepatitis virus, or a lentivirus), an RNA virus (including diseases such as SARS, influenza, hepatitis C, West Nile fever, polio, and measles), a DNA virus (including diseases such as smallpox, chickenpox, and shingles), or a retrovirus (such as including the HIV virus; and including diseases such as AIDS associated with an HIV infection, tumors, and autoimmune disease). In one embodiment, the subject or patient is immunocompromised.

EXAMPLES

Adult C57BL/6 mice orally inoculated with murine RV (EC strain), using a dose 100,000 times that required to infect 50% of mice, resulted in uniform shedding of virus that was readily detectable by ELISA one day post-inoculation (p.i.) and peaked 3-4 days p.i. Such shedding of RV, which is proportional to the degree of infection (Feng et al., *Adv. Exp. Med. Biol.* 412:233, 1997), continued for several days, after which it became undetectable, indicating clearance of the virus. Administration of a single dose of flagellin (FliC isoform) via intraperitoneal (i.p.) injection shortly before oral inoculation temporarily prevented RV infectivity. In contrast, repeated administration of flagellin every second day maintained protection longer, allowing flagellin treatment to cease without subsequent infection from residual RV that had persisted at low levels in the intestinal lumen (FIG. 1A). The capacity of flagellin to completely prevent RV infection was not shared by the quintessential microbial innate immune agonist lipopolysaccharide (LPS). Specifically, while the TLR4 agonist LPS delayed RV infection, even repeat dosing with LPS over a range of doses, including toxic doses (LPS is highly toxic relative to flagellin; see Vijay-Kumar et al., *J. Immunol.* 180:8280, 2008) did not prevent RV infection.

In short, our methods involved, as a mouse model of asymptomatic RV infection, 8-12 week-old mice of various genotypes. The diarrhea model used neonatal (7-day-old) mice. The model of chronic RV infection used immune-deficient RAG1$^{-/-}$ mice. Murine rotavirus EC strain (natural mouse pathogen) was administered intra-gastrically. FliC isoform of flagellin was isolated, HPLC-purified, purity-verified as previously described (Gewirtz et al., *J. Clin. Invest.* 107:99, 2001; Sanders et al., *Eur. J. Immunol.* 39:359, 2009), and administered by intraperitoneal (i.p.) injection. Infectivity was assayed via quantification of fecal RV antigen or RV genomes in tissue by quantitative (q) RT-PCR. The methods are described more fully below.

RV infection induces an adaptive immune response, which is normally required to clear infection (Sen et al., *J. Virol.* 83:10322, 2009). This response correlates with, and is partially mediated by, induction of RV-specific antibodies (Feng et al., *Adv. Exp. Med. Biol.* 412:233, 1997). The prevention of RV infection conferred by flagellin treatment was accompanied by very little elevation in anti-RV specific antibodies. That blockade of RV infection, which would make RV antigen levels very limiting, precludes adaptive immunity may explain why short-term treatments delayed rather than prevented RV infection and, moreover, suggests that the protective effect of flagellin is independent of adaptive immunity. To test this hypothesis, we examined the capacity of flagellin to protect against RV infection in mice that lack mature B and T lymphocytes due to a deficiency in the recombination-activating gene 1 (RAG1) gene (herein, we designate gene deficiency as in text and KO in the drawings). Unlike immune-competent mice, RAG1$^{-/-}$ mice do not clear RV (Jiang et al., *J. Virol.* 82:6812, 2008). This high degree of infectivity, relative to WT mice, and subsequent chronic infection was completely prevented by flagellin treatment (FIG. 1B).

Analogous to young children, infection of neonatal mice with RV causes watery diarrhea (Ball et al., *Science* 272:101, 1996; and Ramig, *Microbial Pathogenesis* 4:189, 1988). Thus, we examined the extent to which flagellin treatment suppresses RV replication in neonatal mice and ameliorates diarrhea. Flagellin treatment markedly reduced the incidence and duration and the active number of days of RV diarrhea (FIG. 1C). Such reduction of diarrhea in flagellin-treated neonatal mice was associated with reduced RV loads in the intestine at the peak of disease (day 3 p.i.) (FIG. 1D). Thus, flagellin prevents RV infection and its clinical consequences. Flagellin treatment also diminishes reovirus load following oral inoculation with this pathogen, suggesting broad antiviral activity.

We next investigated whether flagellin treatment could treat chronic RV infection in immune-compromised mice. While RAG1$^{-/-}$ mice of all ages develop chronic infection following exposure to RV, a high degree of persistent infection is attained by infecting 3-week-old RAG1$^{-/-}$ mice (Jiang et al., *J. Virol.* 82:6812, 2008). Strikingly, flagellin treatment eliminated detectable RV shedding by 2 days post-treatment. Moreover, 10 doses of flagellin treatment over a 20-day period abolished shedding of RV antigens for the entire 150-day time course during which mice were monitored, whereas untreated mice shed virus over their lifetime (FIG. 1E). Accordingly, RV antigens, which were detectable by immunostaining in villus epithelial cells in untreated chronically-infected RAG1$^{-/-}$ mice, were absent in mice treated with flagellin by 24 hours, slightly preceding the complete abatement of viral shedding in feces by 48 hours. Moreover, treatment with flagellin resulted in reduced levels of RV RNA within hours of administration and undetectable levels by 48 hours post-treatment. Use of strand-specific quantitative RT-PCR to quantify ratios of RV NSP3+ and − strands, which reflect replication rates (Fenaux et al., *J. Virol.* 80:5219, 2006), revealed that reduction in levels of RV genomic RNA was preceded by reduction in levels of RV replication (FIG. 1F). In RAG1$^{-/-}$ mice, a substantial degree of replication occurs extra-intestinally, especially in the liver, resulting in hepatitis (Uhnoo et al, *J. Virol.* 64:361, 1990). Indeed, we observed similar levels of RV RNA in the liver relative to the small intestine in untreated, RV-infected RAG1$^{-/-}$ mice. Such levels of RV RNA in the liver were greatly reduced within 24 hours of flagellin treatment and undetectable within 48 hours (FIG. 1G). Similarly, the more modest levels of RV RNA in the spleen in chronically infected RAG1$^{-/-}$ mice were also eliminated by flagellin treatment. These results indicate that flagellin treatment eradicates chronic RV infection in severely immune compromised mice.

Figure 2:
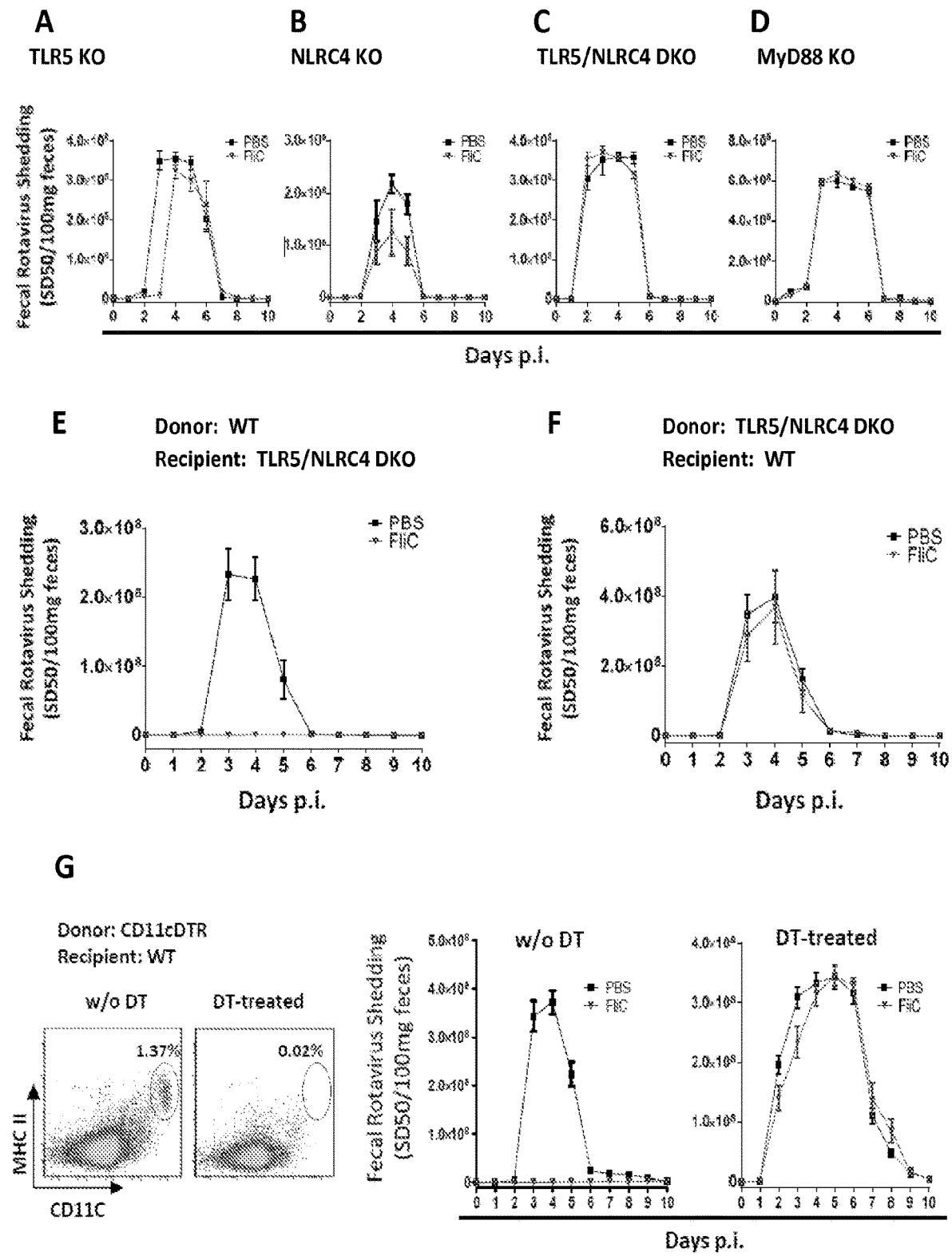
FIGS. 2A-2J are graphs and plots illustrating data indicating that flagellin's antiviral activity is mediated by TLR5/NLRC4 on dendritic cells. Eight-week-old TLR5$^{-/-}$ mice (FIG. 2A; "TLR5 KO"), NLRC4$^{-/-}$ mice (FIG. 2B; "NLRC4 KO"); TLR5/NLRC4$^{-/-}$ mice (FIG. 2C; TLR5/NLRC4 DKO"), and MyD88$^{-/-}$ mice (FIG. 2D; "MyD88 KO") were orally inoculated with murine RV, EC strain. Mice were treated with PBS or flagellin (20 μg) by i.p. injection every second day from 0-8 days p.i. Feces were collected daily and assayed for RV antigens by ELISA. Results in FIGS. 2A-2D are shown as mean+/−S.E.M. [2-way ANOVA, N=5, P<0.05 on days 2-3 in (FIG. 2A), days 3-5 in (FIG. 2B)]. Differences between PBS and flagellin groups in (FIG. 2C) and (FIG. 2D) were not significant [2-way ANOVA, N=4-5, P=0.6361 for (FIG. 2C) and P=0.3871 for (FIG. 2D)]. Bone marrow chimeric mice were inoculated with RV and treated with PBS or flagellin from day 0-8 p.i. Feces were collected daily and assayed for RV antigens by ELISA. Measurements of RV antigens in feces are shown as mean+/−S.E.M. The difference between mice given PBS and flagellin were statistically significant in (FIG. 2E) (2-way ANOVA, N=6-7, P<0.001) and non-significant in (FIG. 2F) (2-way ANOVA, N=5, P=0.4183). CD11c-DTR reconstituted bone marrow chimeras were either untreated or injected with DT at 8 ng/gram body weight once a day for two days. Flow cytometry plots show the extent of depletion of DC-CD45$^+$CD19$^-$ splenocytes gated on MHC Class II and CD11c (FIG. 2G). DT-untreated or DT-treated mice were then given PBS or flagellin injections on day 0-8 p.i. and inoculated with RV. Feces were collected for ELISA to determine virus shedding. The difference between the PBS and flagellin groups was statistically significant in the absence of DT (2-way ANOVA, N=4, P<0.001) and non-significant in DT-treated group (2-way ANOVA, N=6-7, P=0.3821). NLRC4/TLR5$^{-/-}$ mice were adoptively transferred with 4×10$^6$ FACS-sorted DC (purity >98.5%) from NLRC4/TLR5$^{-/-}$ (FIG. 2H) or WT C57BL/6 (FIG. 2I) mice. Twelve hours later, the mice were treated with PBS or flagellin and inoculated with RV. Feces were collected from day 0-10 p.i. and assayed for RV antigens. The difference between the PBS and flagellin groups was statistically significant in (FIG. 2I) (Student's T-test on days 2-4, N=4 P<0.05) but not (FIG. 2H). NLRC4/TLR5$^{-/-}$ mice were adoptively transferred with 20 million MACS-sorted DC (purity >95.0%) from WT C57BL/6 mice, and 12 hours later, the mice were treated with PBS or flagellin and inoculated with RV as above (FIG. 2J). Feces were collected from day 0-10 p.i. and assayed for RV antigens (Student's t-test on days 2-5, N=4, P<0.05).
Figure 2:
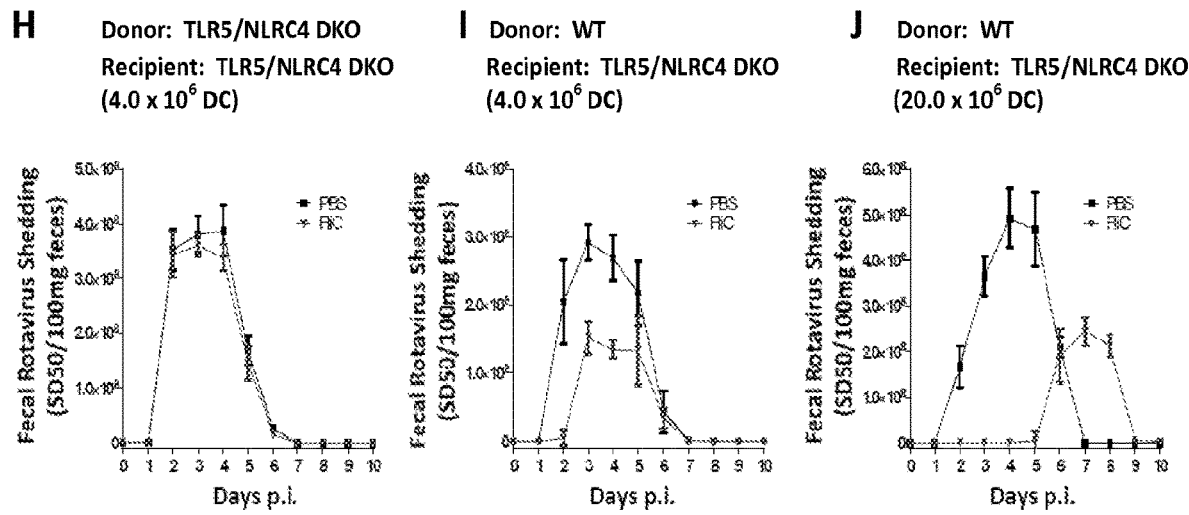

The capacity of systemically-administered flagellin to rapidly remodel intestinal gene expression is dependent on TLR5 (Carvalho et al., *Mucosal Immunol.* 5:288, 2012). In contrast, flagellin can be taken up by some cells and recognized intracellularly by the NLRC4 inflammasome, resulting in caspase 1-mediated production of IL-1β and IL-18 (Kupz et al., *Nature Immunol.* 13:162, 2012; and Vijay-Kumar et al., *Eur. J. Immunol.* 40:3528, 2010). Thus, we expected that only TLR5 would be required for flagellin to protect against RV infection. However, we observed that loss of either pathway of flagellin recognition reduced, but did not completely eliminate, the capacity of flagellin to prevent RV infection (FIGS. 2A and 2B). In contrast, the absence of both TLR5 and NLRC4, namely TLR5/NLRC4$^{-/-}$ (TLR5/NLRC4 DKO in the drawings), or the absence of MyD88, which is required for signaling by TLR5 and inflammasome-associated cytokines, completely eliminated the capacity of flagellin to block RV infection (FIGS. 2C and 2D).

We next sought to define the cell type(s) on which flagellin acts to protect mice from RV infection. First, we considered the possibility that flagellin, which potently activates anti-bacterial gene expression in intestinal epithelial cells, might directly make these cells resistant to RV infection. However, flagellin treatment of cultured epithelial cell lines, which are known to exhibit TLR5-mediated responsiveness to flagellin (Gewirtz et al., *J. Immunol.* 167:1882, 2001; and Gewirtz et al., *J. Clin. Invest.* 107:99, 2001), did not alter RV infection. We generated bone marrow chimeric mice using WT and TLR5/NLRC4$^{-/-}$ mice to determine the extent to which flagellin mediated protection against RV infection requires recognition of flagellin by hemopoietic or non-hemopoietic cells. Transplant of WT bone marrow to irradiated TLR5/NLRC4$^{-/-}$ mice completely restored the capacity of flagellin to prevent RV infection, while administration of TLR5/NLRC4$^{-/-}$ bone marrow to WT mice eliminated flagellin anti-RV activity (FIGS. 2E and 2F). Subsequent use of bone marrow chimeras made from mice lacking only TLR5 or NLRC4 in the hemopoietic or non-hemopoietic compartment confirmed that TLR5 mediation of the flagellin antiviral effect is entirely provided by hemopoietic cell TLR5, while either cell compartment can fulfill the role of NLRC4 in flagellin protection against RV, which is consistent with reports of functional NLRC4 expression in macrophages and in intestinal epithelial cells (Franchi et al., *Nature Immunol.* 7:576, 2006; and Norlander et al., *Mucosal Immunol.* 7:775, 2014). In further accord, flagellin-induced IL-18 production in serum originates from both hemopoietic and non-hemopoietic cells.

We reasoned that immune cells recruited to the intestine in response to flagellin might mediate flagellin antiviral effects. Thus, we defined the cell populations recruited to the intestine in response to flagellin treatment. Flagellin induced robust neutrophil recruitment to the intestine. However, under conditions of near complete elimination of neutrophils, by a neutrophil-depleting antibody, administration of flagellin to chronically infected RAG1$^{-/-}$ mice resulted in clearance of infection within 2 days of flagellin treatment. Concordantly, partial depletion of neutrophils in WT mice (the robust induction of neutrophils over the 10-day course of flagellin treatment resisted full depletion) did not alter the capacity of flagellin to protect against RV infection. These results indicate that neutrophils are not required for the flagellin antiviral effect.

We next considered that resident innate immune cells might mediate protection against RV infection by flagellin. Although NK cells were not recruited to the gut in response to flagellin, given their known antiviral effects, we examined the potential involvement of these cells in flagellin antiviral activity. We observed that antibody-mediated depletion of NK1.1$^+$ cells did not reduce the flagellin antiviral effect. Analogously, partial depletion (about 70%) of intestinal macrophages via clodronate liposomes, did not impair the flagellin antiviral effect, suggesting that these cells are not required. Dendritic cells (DC) mediate intestinal production of anti-bacterial peptides in response to flagellin (Kinnebrew et al., *Immunity* 36:276, 2012). To investigate whether these cells play a role in flagellin antiviral effects, we generated chimeric mice in which bone-marrow derived cells were engineered to express the diphtheria toxin receptor (DTR) under control of the CD11c promoter such that CD11c-expressing cells, primarily DC, could be depleted by administration of diphtheria toxin (DT) (Jung et al., *Immunity* 17:211, 2002). DT administration to WT mice did not impair flagellin's capacity to protect against RV infection. Further, in the absence of DT, chimeric mice were protected against RV infection by flagellin treatment (FIG. 2G). However, administration of DT to the chimeric mice to deplete DC eliminated flagellin-mediated protection against RV infection (FIG. 2G). Next, we investigated whether DC expressing TLR5 and NLRC4 are sufficient for flagellin protection against RV infection. TLR5/NLRC4$^{-/-}$ mice were intravenously administered purified DC (CD19$^-$/MHC Class II$^+$/CD11c$^+$/F4/80$^-$) isolated from WT or, as a control, from TLR5/NLRC4$^{-/-}$ mice. Only the WT DCs were capable of partial restoration of flagellin protection against RV infection (FIGS. 2H and 2I). We reasoned that failure to restore full protection likely reflects the small percentage of cells that migrate to the intestine and hence may not compensate for the function of the large number of DCs that populate this organ. Accordingly, transfer of a greater number of DCs resulted in significantly improved flagellin-mediated protection (FIG. 2J). Together, these results indicate that activation of TLR5/NLRC4 on DCs is necessary and sufficient for flagellin antiviral action.

Figure 3:
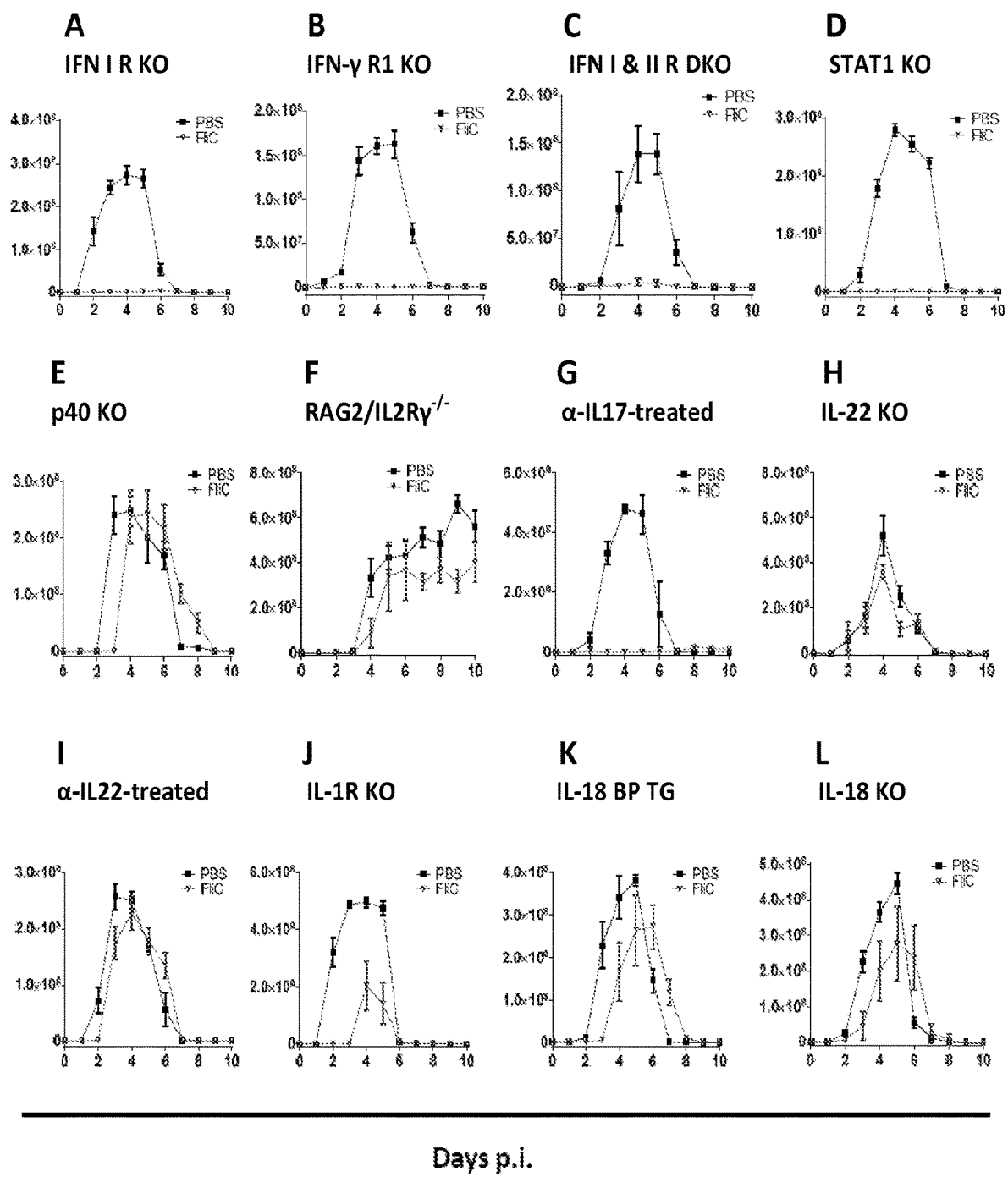
FIGS. 3A-3L are graphs illustrating data indicating that flagellin-mediated protection against RV infection is independent of interferon and requires both IL-22 and IL-18. Indicated strains of genetically-modified 8-week-old mice were orally inoculated with murine RV, EC strain. Mice were treated with PBS or flagellin (20 μg), via injection, every second day from 0-8 days p.i. Feces were collected daily and assayed for RV antigens by ELISA. The following strain was used in each panel.

To gain further insight into the mechanism underlying the flagellin antiviral effect, we determined whether the capacity of flagellin to protect against RV infection involved interferons (IFN), which are induced by RV infection and have potent antiviral effects. However, the flagellin antiviral effect was fully maintained in mice lacking type I and/or II IFN receptors (FIGS. 3A-3C). We also considered the possibility that, like in natural RV infection, flagellin protection against RV infection might involve type III IFN (Pott et al., *Proc. Natl. Acad. Sci. USA* 108:7944, 2011). However, flagellin did not induce intestinal expression of type III IFN or IFN-associated gene expression (Vijay-Kumar et al., *J. Immunol.* 174:6322, 2005). Moreover, in accord with its IFN-independence, flagellin antiviral activity was unaffected by loss of signal transducer and activator of transcription 1 (STAT1) (FIG. 3D), which mediates signaling by IFN and other cytokines with antiviral properties. Such lack of a function for IFN and STAT1 suggests that flagellin prevents and clears RV infection by a previously unrecognized antiviral pathway.

The key role of DC TLR5 in mediating the antiviral action of flagellin suggested to us a function for the IL-12/IL-23 axis, which drives innate lymphoid cells (ILC) to produce IL-17 and IL-22 in response to flagellin (Kinnebrew et al., *Immunity* 36:276, 2012; and Van Maele et al., *J. Immunol.* 185:1177, 2010. In accord with this possibility, RAG2/IL-2Rγ$^{-/-}$ mice, which lack mature B and T cells and ILC, or mice deficient in p40, which is a component of both IL-12 and IL-23, were not effectively protected by flagellin treatment (FIGS. 3E and 3F). Flagellin protection against RV infection was not affected by neutralization of IL-17 (FIG. 3G) but was almost completely abolished by genetic or antibody-mediated blockade of IL-22 (FIGS. 3H and 3I), suggesting a central role for IL-22 in flagellin antiviral action and providing a potential explanation for LPS's limited capacity to protect against RV infection as this agonist does not elicit robust IL-22 production (Zaft et al., *J. Immunol.* 175:6428, 2005). Conversely, the requirement of NLRC4 suggested possible roles for inflammasome cytokines IL-1β and IL-18. Ablation of IL-1 receptor signaling resulted in a modest impairment of flagellin protection against RV infection while blockade of IL-18, achieved by two different genetic models of IL-18 ablation, markedly reduced the flagellin antiviral effect (FIGS. 3J-3L) suggesting a key role for IL-18 in flagellin's antiviral action. In contrast to flagellin-induced IL-22 production, which requires ILC and DC expression of TLR5, flagellin-induced IL-18 production was unimpaired in RAG2/IL-2Rγ$^{-/-}$ or DC-ablated mice demonstrating the distinct signaling events that result in IL-22 and IL-18 production occur in distinct cell types.

Figure 4:
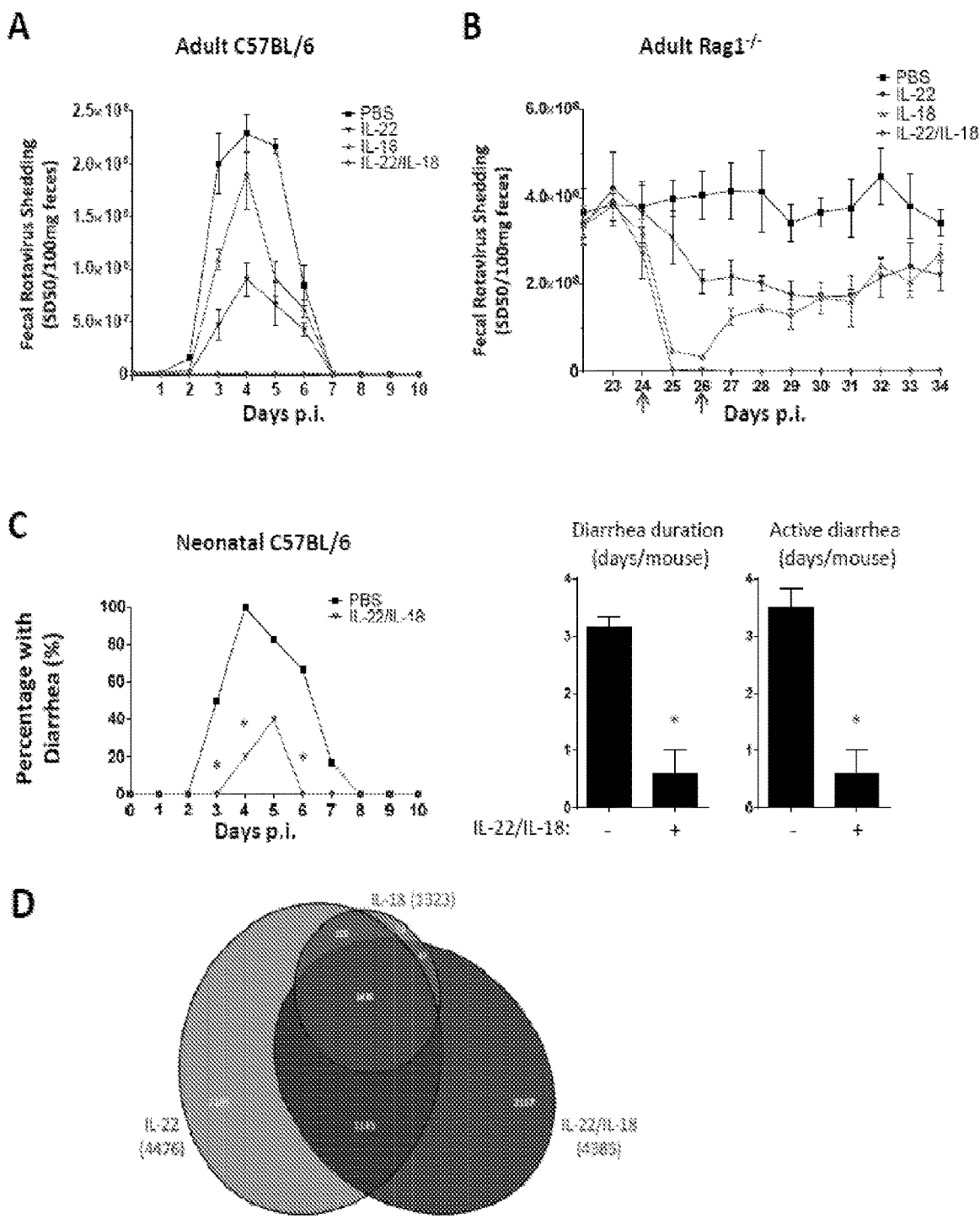
FIGS. 4A-4F are graphs, diagrams, and photomicrographs illustrating data indicating that IL-22/IL-18 treatment prevents and treats RV infection. Adult (eight-week-old) C57/BL6 mice were treated with 0.2 ml PBS (vehicle), or 2 μg IL-22, 1 μg IL-18 or 2 μg IL-22 plus 1 μg IL-18 by i.p. injection and subsequently inoculated with RV. The cytokines injection was repeated every other day from 0-8 days p.i. Feces were collected daily and assayed for RV antigens by ELISA. Results are shown as mean+/−S.E.M. The differences between PBS and IL-22/IL-18 groups are statistically significant (2-way ANOVA, N=4, P<0.0001) (FIG. 4A). RAG1$^{-/-}$ mice, chronically infected with RV, were treated respectively with PBS, 10 μg IL-22, 1 μg IL-18 or 10 μg IL-22 plus 1 μg IL-18 by i.p. injection on day 24 and 26 p.i., as indicated by the two arrows along the X-axis, and assayed for RV antigens by ELISA. The differences between the PBS- and IL-22/IL-18-treated groups are statistically significant (2-way ANOVA, N=4, P<0.0001) (FIG. 4B). Neonatal (seven-day old) C57BL/6 mice were orally inoculated with RV. Mice were treated with 50 μl PBS (vehicle) or 1 μg IL-22 plus 0.2 μg IL-18 immediately before inoculation, and 1-9 days p.i. and monitored for the incidence of diarrhea daily (Chi-square test, N=5-6, *P<0.05). IL-22/IL-18-treated mice exhibited a significantly reduced duration of diarrhea and days of active diarrhea (Student t-test, N=5-6, P<0.001) (FIG. 4C). Chronically RV-infected RAG1$^{-/-}$ mice were treated with 1 injection of PBS, PBS containing 10 μg IL-22, 1 μg IL-18 or 10 μg IL-22 plus 1 μg IL-18. At the indicated time, the mice were sacrificed and intestinal epithelial cells (IECs) were prepared from their small intestines.
Figure 4:
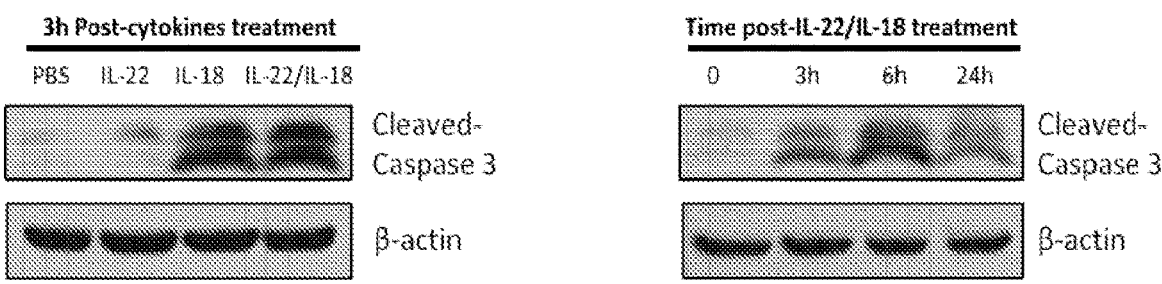
Figure 4:
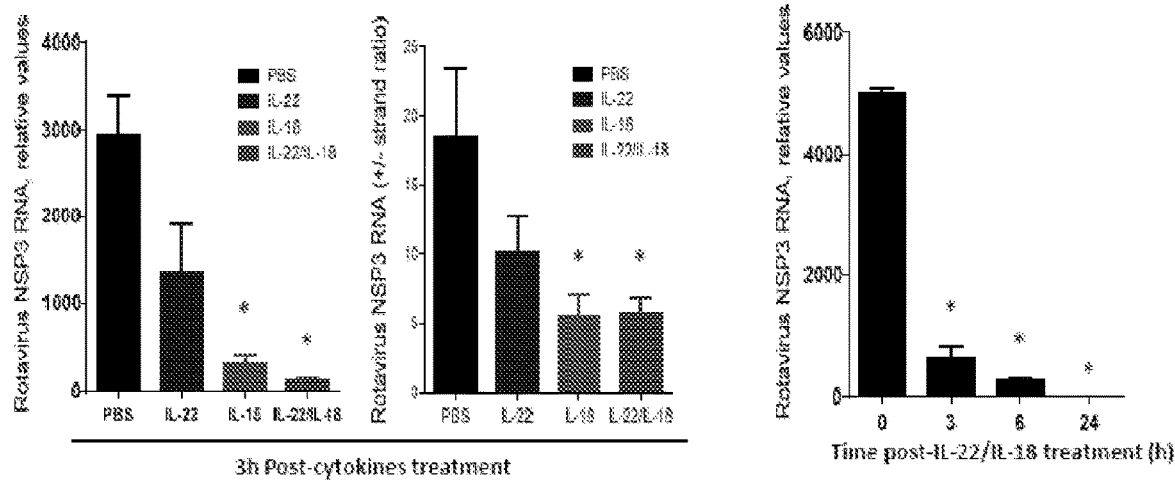

We next investigated the extent to which IL-22 and IL-18 recapitulate flagellin antiviral action. Using the prophylactic model of flagellin-mediated protection against RV infection, we observed that recombinant IL-18 had only modest protective efficacy against RV infection but effectively synergized with the partial protection conferred by administration of recombinant IL-22 resulting in complete protection against a broad range of RV inocula (FIG. 4A). In contrast, administration of IL-18 to mice chronically infected with RV resulted in a rapid and dramatic reduction in RV levels, whereas IL-22 treatment induced only a modest and delayed reduction in RV loads. The rapid effect of IL-18 in reducing RV loads was transient, even with repeat treatment. However, strikingly, the combined action of IL-18 and IL-22 resulted in complete disappearance of RV from these immune-compromised hosts (FIG. 4B). The differential effects of these cytokines in lowering RV titers in acute and chronic infection models was not attributable to cytokine dose in that higher doses of IL-18 did not afford more prophylactic protection nor did higher doses of IL-22 offer greater reduction in RV titers in chronically-infected mice (data not shown). Moreover, these results did not reflect a strong dependence on one of these cytokines for driving the expression of the other in that generation of flagellin-induced IL-18 expression is independent of all TLR5 signaling (Vijay-Kumar et al., *Eur. J. Immunol.* 40:3528, 2010), while flagellin-induced activation of IL-22 (and the IL-12/IL-23 axis) is largely independent of NLRC4 signaling. Rather, our results suggest that parallel signaling pathways activated by IL-22 and IL-18 protect against RV infection and promote clearance of this virus, respectively. Consequently, combined treatment with IL-22 and IL-18 recapitulated the capacity of flagellin to cure RV infection in mice lacking mature T and B lymphocytes. Such combined IL-22/IL-18 treatment eliminated RV from RAG1$^{-/-}$ mice within 24 hours (vs. 48 hours for flagellin) and, in contrast to flagellin, was effective in mice lacking both adaptive immunity and ILC (FIGS. 1E and 4B). Like flagellin, IL-22/IL-18 administration afforded dramatic protection against the severe diarrhea that is the most severe clinical consequence of RV infection (FIG. 4C). Furthermore, treating neonate mice with IL-22/IL-18 after diarrhea manifested shortened this central disease feature. Thus, recapitulating the antiviral effects of flagellin with IL-22/IL-18 might offer broad antiviral therapeutic potential even in the most severely immune compromised hosts.

IL-22/IL-18 treatment did not significantly impede RV infection in cultured IEC. Hence, to investigate mechanisms by which IL-22 and IL-18 treatment cleared RV infection, we examined signaling events in gut epithelial cells isolated from chronically-infected mice treated with IL-22, IL-18, or both cytokines. Analysis of gene expression by RNA sequencing revealed that by 3 hours IL-22 treatment induced a major re-programming of epithelial cell gene expression implicating genes involved in a broad array of cellular processes (FIG. 4D). A much more modest effect on gene expression occurred in epithelial cells isolated from IL-18-treated mice while the combination of IL-22 and IL-18 induced a number of changes in gene expression not seen with either cytokine alone. In contrast, IL-18 but not IL-22 resulted in rapid activation of caspase 3 in epithelial cells of RV-infected mice (FIG. 4E). Thus, IL-22 and IL-18 induced changes in gene expression and caspase 3 activation that correlated with rapid blockade of RV replication and elimination of RV genomes within 24 hours of cytokine treatment (FIG. 4F). Together, these data suggest that IL-18 induces signaling events that lead to a rapid reduction in RV levels, while IL-22 reprograms epithelial cell gene expression resulting in resistance to RV infection.

We provide a striking demonstration of the power of harnessing innate immunity to prevent and treat virus infection. Given the enormous public health burden caused by RV infections, which causes 600,000 deaths per year in children (Parashar et al., *Emerging Infectious Diseases* 12:304, 2006), and can result in chronic infections in immune compromised persons, this strategy present an important therapeutic opportunity presuming inherent differences between human and mouse RV strains (Graff et al., *PLoS Pathogens* 5, e1000280, 2009) do not render it ineffective. Moreover, that, of the hundreds of changes in gene expression induced by flagellin that require both flagellin receptors, the antiviral action of this bacterial product is fully recapitulated by IL-22 and IL-18, which could clear chronic infection in a host lacking innate and adaptive lymphocytes, suggests this combination of cytokines is a means to treat a broad array of chronic viral infections even in severely immune compromised patients. Recapitulating the antiviral action of flagellin with IL-22/IL-18 would also circumvent differences in NLRC4 function between mice and humans (Zhao et al., *Nature* 477:596, 2011). The action of these cytokines would likely be synergistic with therapies that directly target viruses and/or those that promote adaptive immunity. Thus, we propose activation of innate immunity with flagellin, or recapitulation of its antiviral action with IL-22 and IL-18, as a strategy to combat emerging and recalcitrant viral pathogens.

What is claimed is:

1. A pharmaceutical composition comprising a synergistic amount of an interleukin-18 (IL-18) and an interleukin 22 (IL-22), and a pharmaceutically acceptable carrier, wherein the IL-18 consists of a sequence that is at least 95% identical to the sequence of the wild-type human IL-18 and the IL-22 consists of a sequence that is at least 95% identical to the sequence of the wild-type human IL-22; and wherein the synergy is determined relative to the ability of the individual interleukins to modify rotavirus shedding.

2. The composition of claim 1, wherein the IL-18 consists of a sequence that is at least 98% identical to the sequence of the wild-type human IL-18 and the IL-22 consists of a sequence that is at least 99% identical to the sequence of the wild-type human IL-22.

3. The composition of claim 1, wherein the IL-18 or the IL-22 is joined to a heterologous polypeptide that increases the circulating half life of the interleukin to which it is joined.

4. The composition of claim 3, wherein the heterologous polypeptide is an albumin or a portion of an immunoglobulin that lacks an antigen-binding region.

5. The composition of claim 1, wherein the composition is formulated for intravenous administration.

* * * * *